(12) United States Patent
Edwards

(10) Patent No.: US 6,809,231 B2
(45) Date of Patent: Oct. 26, 2004

(54) FLEXIBLE AND ABSORBENT ALGINATE WOUND DRESSING

(75) Inventor: Judson V. Edwards, Mandeville, LA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 150 days.

(21) Appl. No.: 09/989,889

(22) Filed: Nov. 21, 2001

(65) Prior Publication Data

US 2003/0105419 A1 Jun. 5, 2003

(51) Int. Cl.$^7$ ............................................... A61F 13/00
(52) U.S. Cl. .......................................... 602/48; 602/43
(58) Field of Search .................. 602/41–59; 428/283, 428/288, 378, 913; 424/441–449; 514/23

(56) References Cited

U.S. PATENT DOCUMENTS 5,672,418 A * 9/1997 Hansen et al. ............... 428/283
5,700,848 A * 12/1997 Soon-Shiong et al. ......... 522/7
2002/0012693 A1 * 1/2002 Cohen et al. ................ 424/446

FOREIGN PATENT DOCUMENTS

EP         0 440 472 A1 * 7/1991

OTHER PUBLICATIONS

Quinn, K.J., et al., "Principles of Burn Dressings", *Biomaterials*, vol. 6, pp. 369–377, Nov. 1985.
Purna, S.K., et al., "Collagen Based Dressings–A Review", *Burns*, vol. 26, pp. 54–62, 2000.
Lamke, L.O., et al., "The Evaporative Water Loss from Burns and the Water–Vapor Permeability of Grafts and Artificial Membranes Used in the Treatment of Burns", *Burns*, vol. 3 (3), pp. 159–165, 1977.
C. Welch, "Formaldehyde–Free DP Finishing with Polycarboxylic Acids", *American Dyestuff Reporter*, pp. 19–26 & 132, Sep. 1994.
C. Yang, Characterizing Ester Crosslinkages in Cotton Cellulose with FT–IR Photoacoustic Spectroscopy, *Textile Res. Institute*, pp. 298–305, May 1991.
Grinnell, F., et al., "Fibronectin Degradation in Chronic Wounds Depends on the Relative Levels of Elastase, a1–Proteinase Inhibitor, and a2–Macroglobulin", J. Investigative Dermatology, vol. 106, pp. 335–341, 1996.
Morgan, E.D., et al., Ambulatory Management of Burns, *American Family Physician*, vol. 62 (9), pp. 2015–2026, Nov. 1, 2000.
Hirst, E.L., et al., "The Structure of Alginic Acid. Part I.", *J. Chem. Society*, pp. 1880–1885, 1939.

(List continued on next page.)

Primary Examiner—Kim M. Lewis
(74) Attorney, Agent, or Firm—John D. Fado; G. Byron Stover

(57) ABSTRACT

A wound dressing containing cellulose-containing material and alginate, wherein the alginate is crosslinked through a polycarboxylic acid ester bond to the celluose of the cellulose-containing material.

A method for preparing a wound dressing is disclosed wherein alginate is crosslinked to cellulose through a polycarboxylic acid ester bond, comprising introducing cellulose-containing material into an aqueous solution wherein the aqueous solution contains water, alginate, a crosslinker, optionally an acid catalyst, and optionally polyethylene glycol to form cellulose-containing material wherein alginate is crosslinked to cellulose through a polycarboxylic acid ester bond, drying, and curing.

A wound dressing wherein the wound dressing is prepared by the above method.

28 Claims, 6 Drawing Sheets

OTHER PUBLICATIONS

B. Andrews, "Nonformaldehyde DP Finishing of Cotton with Citric Acid", *Textile Chemist and Colorist*, vol. 22(9), pp. 63–67, Sep. 1990.

Edwards, J.V., et al., "Modified Cotton Gauze Dressings that Selectively Absorb Neutrophil Elastase Activity in Solution", *Wound Repair and Regeneration*, vol. 9(1), pp. 50–58, Jan./Feb. 2001.

Yager, D.R., et al., "Ability of Chronic Wound Fluids to Degrade Peptide Growth Factors is Associated with Increased Levels of Elastase Activity and Diminished Levels of Proteinase Inhibitors", *Wound Repair and Regeneration*, vol. 5(1), pp. 23–32, Jan./Mar. 1997.

Goldthwait, C.F., et al., "Semielastic Cotton Gauze Bandage Fabric", *Surgery*, vol. 18(4), pp. 507–510, Oct. 1945.

Le, Y., et al., "Recent Development in Fibres and Materials for Wound Management", *Indian Journal of Fibre & Textile Res.*, vol. 22, pp. 337–347, Dec. 1997.

Edwards, J.V., et al., "Inhibition of Elastase by a Synthetic Cotton–Bound Serine Protease Inhibitor: In Vitro Kinetics and Inhibitor Release", *Wound Repair and Regeneration*, vol. 7(2), pp. 106–118, Mar./Apr. 1999.

* cited by examiner

FLEXIBLE AND ABSORBENT ALGINATE WOUND DRESSING

BACKGROUND OF THE INVENTION

The present invention concerns a wound dressing composed of cellulose-containing material and alginate, wherein the alginate is crosslinked through a polycarboxylic acid ester bond to the celluose of the cellulose-containing material. The present invention also concerns a method for preparing a wound dressing wherein alginate is crosslinked to cellulose through a polycarboxylic acid ester bond, involving introducing cellulose-containing material into an aqueous solution (containing water, alginate, a crosslinker, optionally an acid catalyst, and optionally polyethylene glycol to form cellulose-containing material wherein alginate is crosslinked to cellulose through a polycarboxylic acid ester bond), drying, and curing. The present invention additionally concerns a wound dressing wherein the wound dressing is prepared by the above method.

Burn wound dressings should ideally possess certain properties, including absorbency, ease of application and removal, protection against bacteria, fluid balance, and mechanical characteristics that accommodate movement (Quinn, K. J., et al., Biomaterials, 6(6): 369–377 (1985)). Both cotton gauze and alginate dressings have been used extensively in burn wound care and possess some of these properties. Alginate dressings are suitable for partial- and full-thickness wounds with moderate to heavy exudate and usually do not require frequent dressing changes (Le, Y., et al., Indian Journal of Fibre & Textile Research, 22: 337–347 (1997)). Alginate dressings provide gelation and moist healing which promotes re-epithelialization. Gamgee tissue, which bears the name of its developer, is a form of cotton gauze ("tulle gras" dressings) utilized in burn wound care and is an economical alternative to synthetic dressings; it is a wide mesh gauze impregnated with medical grade paraffin (Purna, S. K., and M. Babu, Burns, 26: 54–62 (2000)). However, both alginate and cotton-based wound dressings also have limitations that make them less than ideal. Although low cost and possessing good tensile properties, readily textiled cotton gauze provides little or no moist healing because it allows rapid evaporation of moisture which results in a dry desiccated wound bed which is a significant issue with burn wounds since water loss tends to occur at a much greater rate even when covered (Samke, L. O., et al., Burns, 3: 159–165 (1977)). Alginate dressings usually require a secondary dressing for application and have little or no elasticity for stretching freely over joints. Thus, the combination of occlusion and gelation with elasticity and conformability in a single wound dressing would provide advantages over current wound dressings.

SUMMARY OF THE INVENTION

A wound dressing containing cellulose-containing material and alginate, wherein the alginate is crosslinked through a polycarboxylic acid ester bond to the celluose of the cellulose-containing material.

A method for preparing a wound dressing wherein alginate is crosslinked to cellulose through a polycarboxylic acid ester bond, involving introducing cellulose-containing material into an aqueous solution (containing water, alginate, a crosslinker, optionally an acid catalyst, and optionally polyethylene glycol to form cellulose-containing material wherein alginate is crosslinked to cellulose through a polycarboxylic acid ester bond), drying, and curing.

A wound dressing wherein the wound dressing is prepared by the above method.

DETAILED DESCRIPTION OF THE INVENTION

Figure 1:
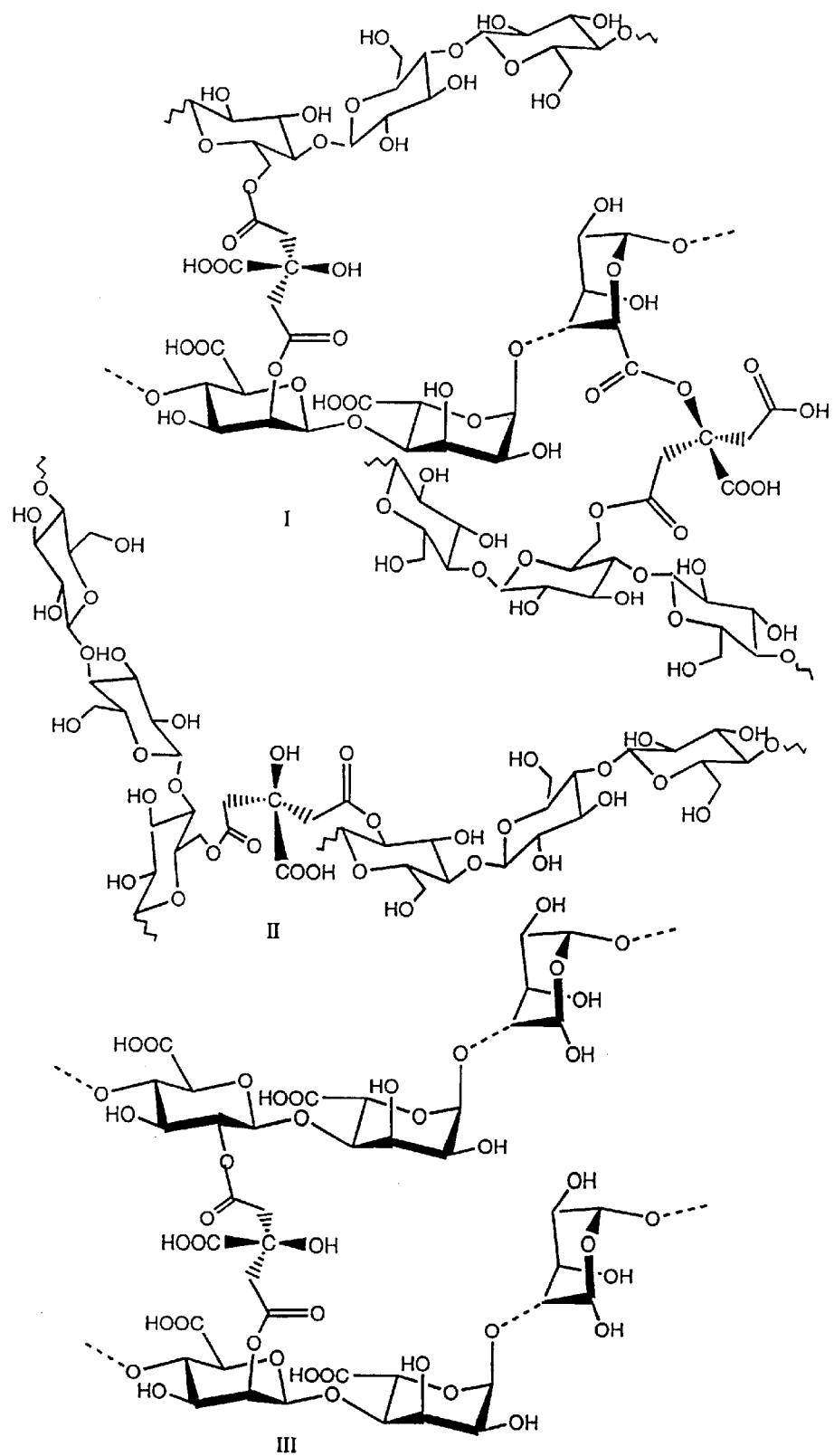
FIG. 1 shows the structure of a citrate-linked algino-cellulose conjugate (Structure I: cellulose linked to alginate; Structure II: cellulose crosslinked to cellulose; Structure III: alginate linked to alginate).

The wound dressings of the present invention comprise an absorbent woven or nonwoven fabric made from any of the cellulose-containing materials which have been previously employed in dressings. In the present invention, alginate is crosslinked to the cellulose of the cellulose-containing material through a polycarboxylic acid ester bond (e.g., through a citrate ester as shown in FIG. 1). Generally, the cellulose-containing material may be any of the following: (a) fibers of cotton gauze (e.g., stretch cotton gauze), or cotton/polyolefin or cotton/polyester blends; (b) cellulose-containing impregnates including pine mesh gauze, paraffin and lanolin-coated gauze, polyethylene-coated gauze, knitted viscose, rayon, and cellulose blends of nylon and polyester; (c) cellulose-containing films, including those of a semipermeable or a semiocclusive nature such as polyurethane copolymers, acrylamides, acrylates, paraffin, polysaccharides, cellophane; (d) cellulose-containing hydrogels such as agar, starch or propylene glycol, which typically contain about 80% to about 90% water and are conventionally formulated as sheets, powders, pastes and gels in conjunction with crosslinked polymers such as polyethylene oxide, polyvinyl pyrollidone, acrylamide, propylene glycol. Preferably commercial cotton gauze may be utilized. The amount of alginate crosslinked to the cellulose of the cellulose-containing material in the wound dressings will generally be from about 1 to about 75% by weight of alginate (e.g., 1–75%), preferably about 40 to about 60% (e.g., 40–60%), more preferably about 45 to about 55% (e.g., 45–55%), and most preferably about 50% (e.g., 50%), and about 10 to about 20% (e.g., 10–20%) with direct esterification.

Alginate, as used herein, means pharmaceutically acceptable cationic alginate such as calcium, sodium, potassium, or ammonium alginates.

Generally, the process used to prepare the wound dressing involves treating (e.g., immersing, soaking) the cellulose-containing material (e.g., cotton gauze) in an aqueous solution containing alginate and other reagents (e.g., a crosslinker (which crosslinks the alginate and cellulose), optionally an acid catalyst, and optionally polyethylene glycol). Liquid is removed from the material and the material is then dried; for example, the material can be passed through squeeze rolls set at a pressure of about 10 to about 80 psi (e.g., 10–80 psi), preferably about 50 to about 70 psi (e.g., 50–70 psi), more preferably about 60 psi (e.g., 60 psi), suspended from a horizontal wire in a forced draft oven and dried for about one to about eight minutes (e.g., one-eight minutes), preferably about four to about six minutes (e.g., four-six minutes), most preferably about five minutes (e.g., five minutes) at about 55° to about 95° C. (e.g., 55°–95° C.), preferably about 80° to about 90° C. (e.g., 80°–90° C.), more preferably about 85° C. (e.g The material is initially soaked with the aqueous solution on the face side and run through the padder with a pressure setting of about 10 to about 80 psi (e.g., 10–80 psi), preferably about 50 to about 70 psi (e.g., 50–70 psi), more preferably about 60 psi (e.g., 60 psi), the material is then flipped to the backside and rotated such that the end of the material passes through the aqueous solution in a cyclical fashion; the material is then placed on pin frames where it is dried for about one to about eight minutes (e.g., one-eight minutes), preferably about four to about six minutes (e.g., four-six minutes), most preferably about five minutes (e.g., five minutes), at about 55° to about 95° C. (e.g., 55°–95° C.), preferably about 80° to about 90° C. (e.g., 80°–90° C.), more preferably about 85° C. (e.g., 85° C.), and then cured at about about 140° to about 160° C. (e.g., 140°–160° C.), preferably at about 155° C. (e.g., 155° C.), for about 60 to about 110 second (e.g., 60–110 seconds), preferably about 80 to about 100 seconds (e.g., 80–100 seconds), more preferably for about 90 seconds (e.g., 90 seconds).

The alginate concentration in the aqueous solution is generally about 1 to about 2 gm alginate/100 mL (e.g, 1–2 gm alginate/100 mL), preferably about 1 to about 1.5 gm alginate/100 mL (e.g, 1–1.5 gm alginate/100 mL), or more preferrably about 1 gm alginate/100 mL (e.g, 1 gm alginate/100 mL). The crosslinker (e.g., citric acid) concentration in the aqueous solution is generally about 0.1 to about 1 M (e.g., 0.1–1.0 M), preferably about 0.4 to about 0.8 M (e.g., 0.4–0.8 M), or more preferably about 0.62 M (e.g, 0.62 M). The crosslinker is a non-toxic (i.e., biologically compatible with wounds) polycarboxylic acid such as citric acid (preferred), maleic acid, itaconic acid, succinic acid, trans-aconitic acid, cis-aconitic acid, tricarbalyllylic acid, 1,2,3,-benzenetricarboxylic acid, 1,2,4-benzenetricarboxylic acid, 1,2,3,4-butanetetracarboxylic acid, 1,2,3,4-cyclobutanetetracarboxylic acid, all-cis-1,2,3,4-cyclopentanetetracarboxylic acid, tetrahydrofuran-2,3,4,5-tetracarboxylic acid, 1,2,4,5-benzenetetracarboxylic acid, all-cis-1,2,3,4,5,6-cycohexacarboxylic acid, mellitic acid, or polymaleic acid. The acid catalyst concentration in the aqueous solution is generally about 1 to about 10% (e.g, 1–10%), preferably about 2 to about 6% (e.g, 2–6%), more preferably about 4% (e.g., 4%)). The acid catalyst may be lithium hydrogen phosphate, sodium hydrogen phosphate, potassium hydrogen phosphate, lithium hydrogen phosphate, sodium hydrogen phosphate, potassium hydrogen phosphate, sodium phosphate, sodium carbonate, calcium hydrogen phosphate, sodium hypopbosphite (preferred), or sodium phosphite. The polyethylene glycol concentration in the aqueous solution is generally about 1 to about 50% (e.g., 1–50%), preferably about 1 to about 4% (e.g., 1–4%), more preferably about 1.2% (e.g., 1.2%). The polyethylene glycol may be polyethylene glycol 200, 400, 600 (preferred), 1500, 4000, or 6000.

As noted above, the polycarboxylic acid may be citric acid. The attachment of alginate to citrate esters of cellulose proceeds through formation of a polycarboxylic acid ester bond with both alginate and cellulose. Formation of this bond may form to link the aglinate to the cellulose and to also form crosslinks between neighboring cellulose strands and alginate strands. In addition it may result in the formation of an alginate film that is deposited and covalently linked to the cellulose fibers. This same chemical reaction may be performed on any cellulose-containing fiber possessing hydroxyl groups which may form an ester bond to a polycarboxylic acid.

The wound dressings may be in the form of swabs, wound pads, ribbons, sponges, nets and bandages and may be used as a primary or secondary dressing.

The algino-cellulose dressing can also be formulated to contain other compounds, such as antiseptics, analgesics or other medicaments. More specifically, a non-toxic elastase inhibitor (e.g., oleic acid) may be embedded in the fiber during the finishing process. The potential of embedding an elastase inhibitor in the cotton fiber for control of destructively high protease levels in the chronic wound has been previously demonstrated (Edwards, J. V., et al., Wound Repair and Regeneration, 7: 106–118 (1999)). The application of oleic acid as an elastase inhibitor to the fibers of wound dressings provides a route to the release of protease inhibitors into the chronic wound.

As shown below, for example, cotton-based alginate wound dressings were prepared with a method that gave rise to a novel modified cotton gauze having properties that are advantageous to bum wound care. The gauze contains an algino-cellulose conjugate that gels upon hydration while retaining elasticity. The algino-cellulose dressing combines the conforming stretch properties of a cotton gauze with the properties of occlusive wound dressings. Occlusive wound dressings create moist wound healing conditions by transmitting gases and water vapor from the wound surface to the atmosphere and maintain high humidity in the wound (Wiseman, D. M., et al., Wound dressings: design and use, IN: Wound healing: biochemical and clinical aspects, Cohen, I. K., Diegelmann, R. F., Lindblad, W. J., editors, Philadelphia, Saunders, 1992, pages 562–80).

The following examples are intended only to further illustrate the invention and are not intended to limit the scope of the invention as defined by the claims.

EXAMPLES

Materials and Methods:

Cotton gauze samples: Gauzes used in this study were obtained from a commercial source. Type III cheesscloth was subject to slack mercerization. Type III cheesecloth was placed in a 20% solution of sodium hydroxide for 10 minutes. After that time, the cloth was rinsed under running tap water to pH 8. Excess water was removed from the fabric and it was allowed to air dry before additional treatments.

Treatment to form citrate and alginate crosslinking: Gauze samples were treated with from 1–3 gm/100 mL of Na alginate (Keltone HCVR, Monsanto Pharmaceutical Ingredients, San Diego Calif.). The gauzes were immersed in an aqueous padding solution of the alginate and other reagents used in the treatments such as 0.62 M citric acid, 4.0% sodium hypophosphite, and 1.2% polyethylene glycol (Welch, C. M., Formaldehyde-Free DP Finishing with Polycarboxylic Acids, American Dyestuff Reporter, September 1994, pages 19–26). Samples were soaked with this aqueous padding solution on the face side and run through a padder with a 60 psi pressure setting; the samples were then flipped to the backside and rotated such that the opposite end of the fabric passed through solution and then passed through squeeze rolls set at a pressure of 60 psi. The samples were then suspended from a horizontal wire in a forced draft oven and dried for five minutes at 85° C. and then cured at 155° C. for 90 seconds.

Treatment of citrate-crosslinked cotton gauze with alginate: To show the direct crosslinking of alginate onto citrate-cellulose esterified cotton, citrate crosslinked gauze was prepared by immersing the gauze in an aqueous solution of 0.62 M citric acid, and 4.0% sodium hypophosphite (Welch, C. M., Formaldehyde-Free DP Finishing with Polycarboxylic Acids, American Dyestuff Reporter, September 1994, pages 19–26). Samples were soaked with this aqueous padding solution and run through the padder with a 60 psi pressure setting The gauzes were suspended from a horizontal wire in a forced draft oven and dried for five minutes at 85° C. and then cured at 155° for 90 seconds. The resulting citrate crosslinked gauzes were immersed in a 1 gm/100 mL solution of alginate and ran through the padder with a 60 psi pressure setting; the samples were then flipped to the backside and rotated such that the opposite end of the fabric passes through the solution and then passed through squeeze rolls set at a pressure of 60 psi. The samples were suspended from a horizontal wire in a forced draft oven and dried for five minutes at 85° C. and then cured at 155° C. for 90 seconds. Citric acid was utilized in all the finishes and acid catalyst and PEG was utilized in selected finishes.

Samples optionally formulated with oleic acid were immersed in solutions containing varying concentrations of oleic acid (130 mg/100 mL) in an alginate ethanol solution (1 gm/100 mL) and 0.62 M citric acid with 4% sodium hypophosphite. Gauzes treated with oleic acid were hand squeezed to remove unbound treatment solution whereupon they were dried for five minutes at 85° C. and then cured at 155° C. for 90 seconds.

Absorbency: Gauze samples were tested for their water absorbency by placing weighed samples in a 1.0 M calcium chloride solution for five hours. The samples were then placed on a mesh screen and excess water was removed by pressing the samples on blotter paper. Samples were weighed and the absorbency calculated from the following equation:

percent water absorbed=$A-B/B \times 100$ where $A$=weight of specimen after test and $B$=weight of original specimen.

Enzyme Assays: Treated and untreated gauze samples were submerged in 1 mL of buffer containing 1 unit/mL of human neutrophil elastase. The samples were allowed to incubate for one hour at room temperature, and the gauze samples were removed and placed in an Autovial press filter (Whatman) to drain unbound buffer and enzyme. The unbound elastase fractions were combined and assayed for elastase activity as described below.

Enzyme assays of the solutions containing unbound human neutrophil elastase were conducted in pH 7.6 buffer composed of 0.1M sodium phosphate, 0.5 M NaCl, and 3.3% DMSO and subjected to spectrophotomeric measurement of the release of p-nitroaniline at 410 nm from the enzymatic hydrolysis of N-methoxysuccinyl-Ala-Ala-Pro-Val-p-nitoranilide (Sigma)(Goldthwait, C. F., et al., Surgery, 18(4): 507–510 (October 1945)). The spectrophotometric kinetic assays were performed in a Bio-Rad Microplate Reader (Hercules, Calif.) with a 96-well format. Two hundred microliter aliquots of an elastase solution (0.2 units) were assayed per well, and 20 microliters of a 60 micromolar substrate solution was added to initate the enzyme reaction.

Infrared spectroscopic measurements: A Nicolet Magna—IR 550 spectrometer was used for the FT-IR measurements. Resolution for all infrared spectra was 2 cm$^{-1}$ and 250 scans for each spectrum. The finished cotton gauzes analyzed were ground in a Wiley mill to pass a 80 mesh screen. IR spectra were taken of cotton powder samples prepared 5% by weight in potassium bromide pellets.

Results:

The gauze finishes employed in this study were composed of alginate crosslinked to cotton cellulose using an acid-catalyzed reaction with citric acid as the crosslinking agent. The algino-cellulose structural modifications shown in FIG. 1 were designed based on the citric acid crosslinking. Ester crosslinking may occur between the citric acid carboxyls and cellulose and alginic acid hydroxyls or the alpha-hydroxyl group of citric acid and a carboxyl of alginic acid. Conditions were explored to determine the maximum percent alginate weigh gains achievable while still retaining the stretch properties of gauze.

Figure 2:
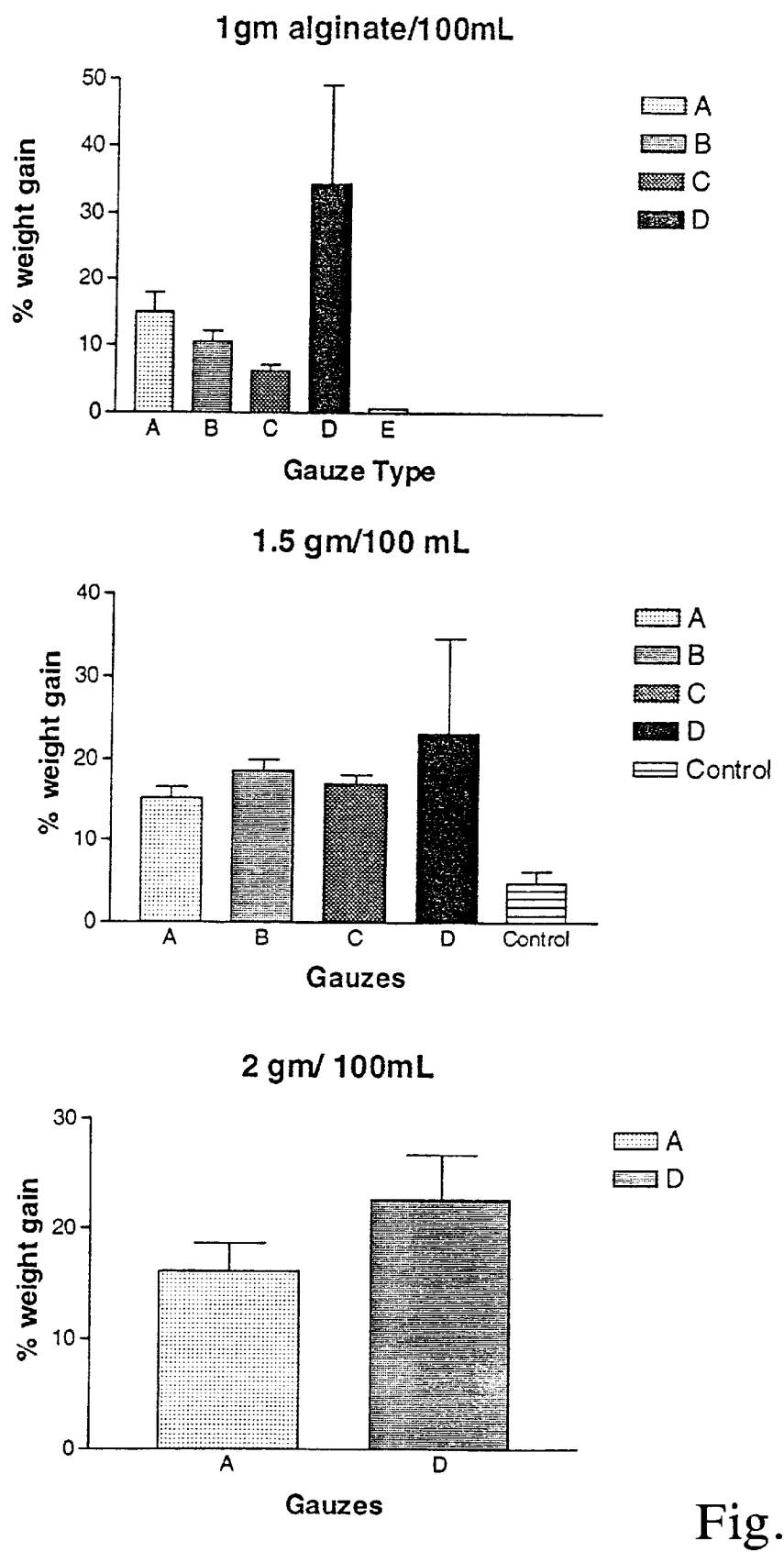
FIG. 2 shows percent weight gains for alginate wound dressings with four types of gauze (Gauze A: 12 ply–4 in.×4 in., USP Type VII gauze, Kendall, Healthcare Products, Mansfield Mass.; Gauze B: Sof-Band bulky bandage, Johnson & Johnson; Gauze C: Kling conforming gauze bandage, Johnson & Johnson; Gauze D: Cheesecloth (cotton) Type III, American Fiber & Finishing Inc, Albemarle, N.C., wherein the cheesecloth was mercerized as described below; gauzes were treated with alginate solutions (1–2 gm/100 mL), as described below, wherein citric acid solutions (0.62M) were combined with sodium hypophosphite solutions (4.0%).

A comparison was made of percent weight gain resulting from the alginate formulations with four types of gauze. The percent weight gain is a reflection of the amount of alginate/citric acid crosslinked to the cotton gauze since excess and unreacted alginate is washed away in the process wash (after the curing step the gauze was washed under a faucet and air-dried). The reagents included citric acid and sodium hypophosphite as the cellulose-alginate crosslinker and acid-catalyst respectively. The results of this study are shown in FIG. 2. Variation in the alginate concentration was assessed as were differing reagent conditions of catalyst and polyethylene glycol. A wide range of percent weight gains was observed based on the alginate concentration, the reagents employed, and the type of gauze treated. Since the viscosity of the alginate solution is too great when it exceeds 2 gm/100 mL, and in order to permit adequate coverage of the gauze, a range of concentrations were employed (including 1 gm/100 mL, 1.5 gm/100 mL and 2 gm/100 mL). Alginate concentrations of 1.5 gm/100 mL gave consistently higher weight gains. Mercerized cheesecloth demonstrated a significantly higher percent weight gain compared with the other three gauze types.

Figure 3:
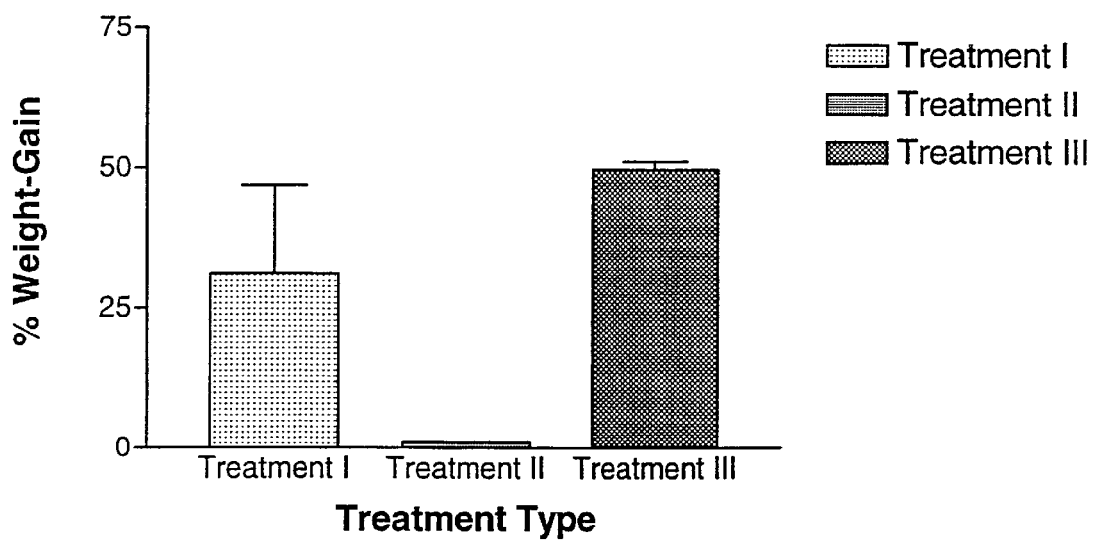
FIG. 3 shows percent weight gains for alginate wound dressings using three types of treatment (all treatments were performed as outlined below: Treatment I included a 0.62 M citric acid solution with 1.5 gm/100 mL alginate, Treatment II included a 4.0% sodium hypophosphite solution with 0.62 M citric acid with 1.5 gm/100 mL alginate, and Treatment III included a 4.0% sodium hypophosphite solution with a 0.62 M citric acid solution with 1.5 gm/100 mL alginate and a 1.2% solution of polyethylene glycol).

A comparison of weight gain for different treatments is seen in FIG. 3. Formulations containing polyethylene glycol, which was added to prevent yellowing of the fabric, gave the highest weight gains. Treatment I with citric acid in the absence of sodium hypophosphite gave a relatively high percent weight gain compared with Treatment II which used sodium hypophosphite in the presence of citric acid.

When citrate esterified cotton gauze was reacted directly with alginate following citrate crosslinking, the alginate weight gain was approximately 10%. This demonstrated that a significant level of direct crosslinking of alginate occurred by esterification of alginate to the citrate carboxyls on cotton cellulose.

Figure 5:
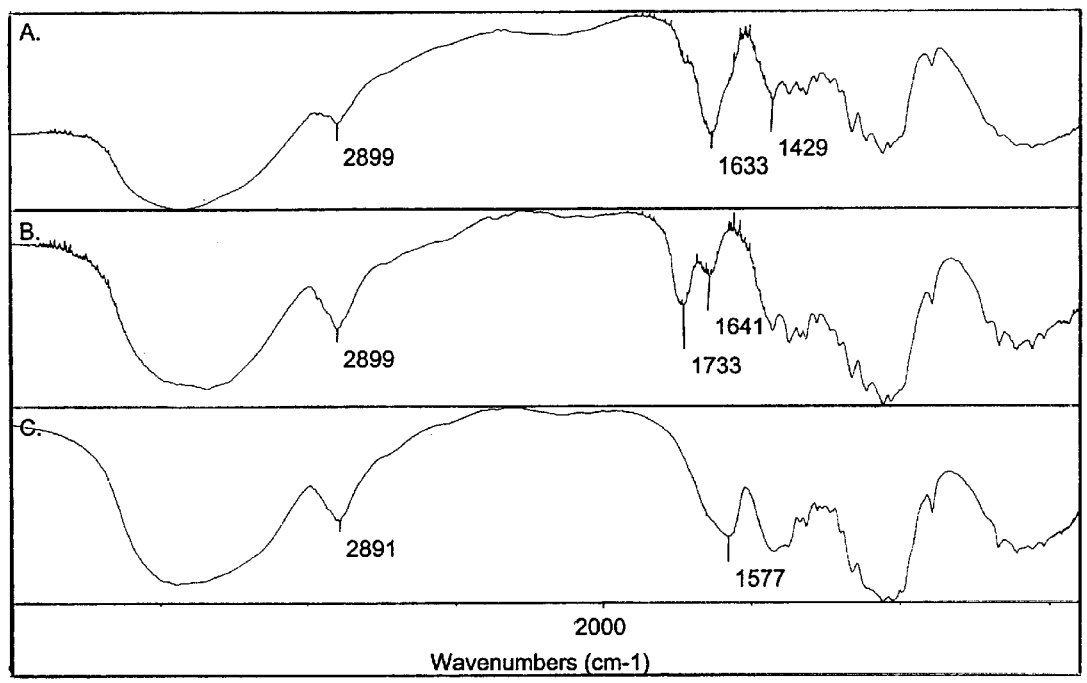
FIG. 5 shows Fourier transform infrared spectra of alginate-citrate conjugate of cellulose on gauze with acid and base treatments: (A) spectrum of crosslinked citrate-alginate on gauze, (B) spectrum of crosslinked citrate-alginate treated with a 0.1 M HCl solution, and (C) treated with a 0.1 M NaOH solution;.

Esterification of alginate was further characterized by FT-IR spectral analysis. When esterification occurs between cotton cellulose and a polycarboxylic acid the carbonyls present in the modified cellulose occur as ester, carboxylic acid, and carboxylate anion functionalities. Therefore the FT-IR of cotton containing the alginate crosslinked to cotton cellulose was used to show that the spectral band of the ester carbonyl can be separated from the bands of the other two carbonyls. This was done by using FT-IR to study the hydrolysis of the ester linkages. The alginate treated cotton gauze was treated with 0.1 M NaOH for two minutes at room temperature. The resulting spectrum of this sample is shown in FIG. 5C. The alginate treated cotton gauze was treated with 0.1 M HCl for two minutes at room temperature. The resulting spectrum of this sample is shown in FIG. 5B. In spectrum B an increase in the band at 1733 $cm^{-1}$ and a decrease in the band at 1633 $cm^{-1}$ is associated with the acid treatment. In spectrum C an increase in the 1576 $cm^{-1}$ band intensity is associated with the base treatment. The band at 1577 $cm^{-1}$ is due to the carbonyl of the carboxylate anions, and the carbonyls of the carboxylic acid and ester overlap are at 1733 $cm^{-1}$ (Yang, C. Q., Textile Research Journal, 61: 298–305 (1991)).

Data regarding absorbency and elasticity are summarized in Table 1. Gauzes A–C are commercial cotton gauzes. Gauze D was prepared through mercerization of cheesecloth, which confers stretch properties to gauze (Goldthwait, C. F., et al., Surgery, 18(4): 507–510 (October 1945)). Among the four modified gauzes tested, elasticity was found to be retained in gauzes A, C, and D. Although there was some retention in elasticity, an approximate 15% loss in elongation was observed in gauze B (a commercial bulky stretch gauze). However, a six-fold increase in absorbency was observed for gauze B, which demonstrated the highest increase in absorbency among the algino-cellulose treated gauzes tested. A 3–4-fold increase in absorbency was observed for gauze C and A. Gauze D (mercerized cheesecloth) revealed a 26% improvement in absorbency. No polyethylene glycol was employed in gauzes in Table 1.

Figure 4:
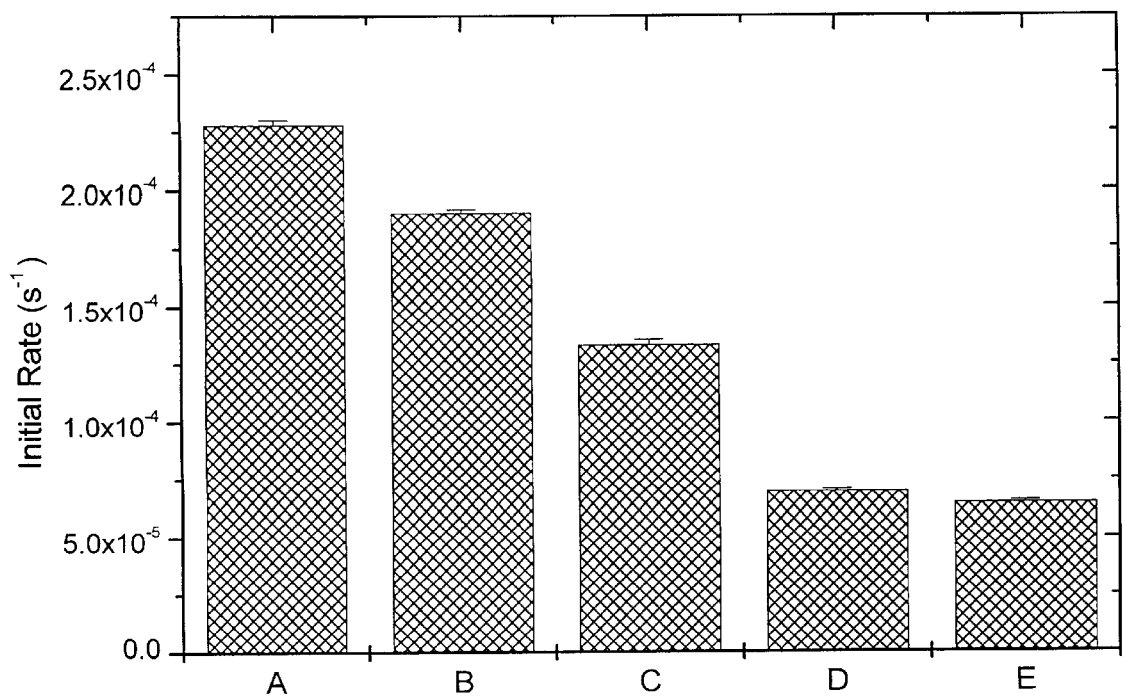
FIG. 4 shows initial velocities ($v_o$) for solutions of elastase taken from oleic acid—treated gauze samples (C–E), untreated gauze (B), and blank elastase solutions containing no gauze (A). Concentrations were 46 mg oleic acid/gm gauze (C) and 84 mg oleic acid/gm gauze (D) prepared with citric acid crosslinking and 84 mg oleic acid/gm gauze (E) prepared with citric acid and sodium hypophosphite crosslinking. A dose response is demonstrated by the concentration dependent lowering of elastase activity. Treated gauze were soaked in 1.2 mL solutions of elastase (0.2 units/mL) for an hour, gauze were pressed dry and the unretained enzyme solutions assayed by spectrophotometric monitoring of substrate hydrolysis. The weight of the gauze samples was 75 milligrams. Gauze samples containing oleic acid were prepared as outlined in the Materials and Methods section at a concentration of 130 mg/100 mL, oleic acid ethanol solution (C). The finishing formulation also consisted of citric acid and alginate; 260 mg/100 mL and 130 mg/mL oleic acid (D & E) ethanol solution where the formulation consisted of citric acid, sodium alginate and sodium hypophosphite.

The present study employed a well-characterized elastase inhibitor, oleic acid, to demonstrate that its inclusion in a finishing formulation, as a fiber-bound inhibitor, will give a lowering of elastase activity. Recent findings that proteases such as neutrophil elastase are present in high levels in both burn wounds and chronic pressure ulcers suggest that these proteases may impede wound healing by degrading fibronectin, extracellular matrix proteins, peptide growth factors, and cell surface receptors (Grinell, F., et al., J. Invest. Dermotol., 103: 155–161 (1994); Yager, D. R., et al., Wound Repair Regen., 5: 23–32 (1997)). The algino-cellulose treated gauze was formulated with the elastase inhibitor oleic acid during the alginate application and curing process. To assess the ability of the oleic acid treated gauze to lower elastase activity, gauze samples and untreated gauze were placed in a solution of elastase. The elastase activity present in the treated gauze solution was compared with the activity of untreated gauze solution. The rates of enzyme catalyzed substrate hydrolysis are reported as initial velocities ($v_o$) in FIG. 4. Finishing formulations containing a citric acid crosslinked alginate with oleic acid were found to inhibit neutrophil elastase activity.

Discussion:

Dressings for burn wounds are usually selected for patient care based on the depth and pathology of the wound. Burn wounds are categorized into four types with the traditional first, second, and third degree classification now being replaced by superficial, superficial partial thickness, deep partial thickness, and full thickness (Morgan, E. D., et al., American Family Physician, 62(9): 2015–2026 (November 2000)). Burn wound dressings may be categorized as conventional, biological, and synthetic (Quinn, K. J., et al., Biomaterials, 6(6): 369–377 (1985)). The preferred biological wound dressing is skin, and with a split thickness skin graft full thickness skin loss may heal within a few days. However, conventional or synthetic wound dressings are often utilized as an interim application. Since both deep partial thickness and full thickness wounds are highly exudative, alginate-based wound dressings are often used. Cotton wool, gauze, lint and Gamgee are used for burns with the biggest advantages being elasticity and absorptive capacity. The algino-cellulose wound dressings described herein showed improved absorptive capacity while retaining elasticity and gelling properties that provide a moist healing environment and facilitates ease of dressing removal.

Figure 6:
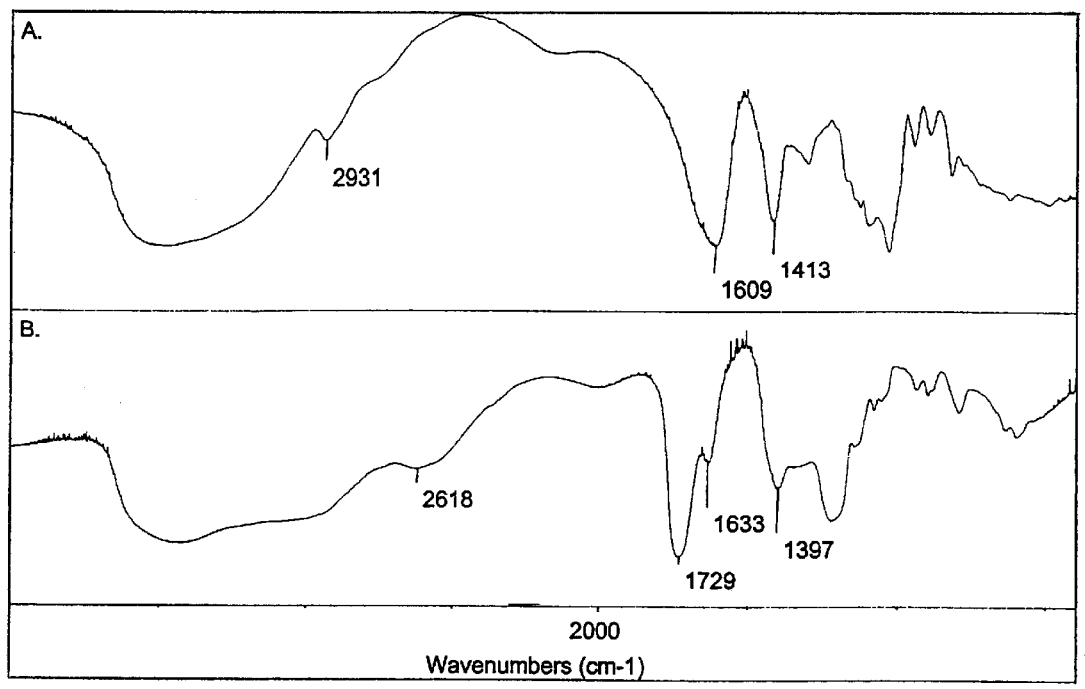
FIG. 6 shows Fourier transform infrared spectra of alginate-citrate conjugate film: (A) spectrum of sodium alginate (neat) and (B) spectrum of alginate-citrate film (sodium chloride plate).

Alginate was formulated, for example, onto cotton gauze to give a durable dressing with both elasticity and occlusive properties. The result of this formulation was to enhance the properties of cotton gauze. Formulation of the crosslinking ester bond may occur between the cellulose and alginate or within the cellulose or alginate macromolecules as either intermolecular or intramolecular crosslinking between and within the two biopolymers. When alginate finishing formulations were subject to curing temperatures identical to those for application to the gauze, formation of transparent films was observed. However, the films were too fragile to test for strength and elongation. The IR spectra of alginate and the alginate-citrate film are shown in FIG. 6. The IR spectrum of the sodium salt of alginic acid (spectrum A) was compared with that of the algino-citrate film (spectrum B) formed from the polymerization reaction of alginic acid and citrate. In spectrum A, a strong asymmetrical stretching band at 1609 $cm^{-1}$ and a weaker, symmetrical stretching band near 1400 $cm^{-1}$ is indicative of the carboxylate ion of alginate. In spectrum B, the carbonyl band at 1729 $cm^{-1}$ of the carboxylic acid and ester overlap formed as a result of citrate crosslinking to aglinic acid.

Alginate is a naturally occurring polysaccharide derived from brown seaweed (Hirst, E. L., et al., Structure of alginic acid, Part I, J. Chem Soc., 1880–5 (1939)). Alginate fibers have been used in the production of high tech wound dressings that can interact with wound exudate to form a moist gel. The intention described herein created a gelling surface on stretch cotton gauze to provide non-adherent occlusion at the dressing and wound interface. Alginate co-polymers contain L-guluronic acid (G) and D-mannuronic acid (M) arranged in three types of blocks (GG, MM, and MG). Alginate forms a gel when the divalent metal ion calcium binds with GG and water is sequestered between the polymer chains. The algino-cellulose wound dressings of this study were renatured with calcium to provide a moist gelling surface on the gauze. Ion exchange of calcium with sodium upon contact with a wound draws water into the alginate fiber and results in swelling and contouring to the wound surface. Alginate fibers with high M content can be easily removed from the wound surface without disruption of delicate tissue. Thus the attachment of alginate to cotton gauze provides some non-adherent properties to facilitate dressing removal from the wound.

Previously the use of formulating elastase inhibitors onto cotton fibers has been introduced as a method of reducing high levels of elastase in the chronic wound (Edwards, J. V., et al., Wound Repair and Regeneration, 7: 106–118 (1999)). Application of a non-toxic fatty acid elastase inhibitor during a gauze finishing formulation allowed the inhibitor to be embedded in the crosslinked fiber with retention of activity. Assessment of the elastase-lowering activity with the oleic acid treated algino-cellulose gauze under solution conditions that mimic the wound environment revealed a decrease in elastase activity.

The present study focused on the design and preparation of a cotton-based alginate wound dressing which possesses enhanced absorbency and stretch properties. Burn wound dressings should have several properties. The present wound dressing was designed with the goal of developing a highly absorbent dressing that will adhere to wounds where joint motion needs to be accommodated while promoting moist wound healing. Ease of application and removal of the dressing from the wound should ideally be accompanied by comfort, conformability, durability, and elasticity. The improved absorption properties of this wound dressing design where alginate was combined with stretch cotton suggests that it will absorb fluid, control its transmission, and maintain a high humidity at the wound, which should encourage more rapid epithelialization. Finally, the wound dressing design reported herein should also give some capability of drug delivery. Elastase inhibitor formulations on fibers having these properties may result in preventing degradation of fibronectin and important growth factors necessary for tissue regeneration by restoring the protease antiprotease imbalance in the nonhealing wound.

All of the references cited herein are incorporated by reference in their entirety.

Thus, in view of the above, the present invention concerns (in part) the following:

A method for preparing a wound dressing wherein alginate is crosslinked to cellulose through a polycarboxylic acid ester bond, comprising or consisting essentially of or consisting of introducing cellulose-containing material into an aqueous solution wherein said aqueous solution comprises (or consists essentially of or consists of) water, alginate, a crosslinker, optionally an acid catalyst, and optionally polyethylene glycol to form cellulose-containing material wherein alginate is crosslinked to cellulose through a polycarboxylic acid ester bond, drying, and curing.

The above method, wherein said alginate is selected from calcium alginate, sodium alginate, potassium alginate, ammonium alginate, and mixtures thereof.

The above method, wherein said alginate is sodium alginate.

The above method, wherein said crosslinker is a polycarboxylic acid selected from the group consisting of citric acid, maleic acid, itaconic acid, succinic acid, trans-aconitic acid, cis-aconitic acid, tricarbalyllylic acid, 1,2,3,-benzenetricarboxylic acid, 1,2,4-benzenetiicarboxylic acid, 1,2,3,4-butanetetracarboxylic acid, 1,2,3,4-cyclobutanetetracarboxylic acid, all-cis-1,2,3,4-cyclopentanetetracarboxyli acid, tetrahydrofuran-2,3,4,5-tetracarboxylic acid, 1,2,4,5-benzenetetracarboxylic acid, all-cis-1,2,3,4,5,6-cycohexacarboxylic acid, mellitic acid, polymaleic acid, and mixtures thereof.

The above method, wherein said crosslinker is citric acid.

The above method, wherein said acid catalyst is selected from the group consisting of lithium hydrogen phosphate, sodium hydrogen phosphate, potassium hydrogen phosphate, lithium hydrogen phosphate, sodium hydrogen phosphate, potassium hydrogen phosphate, sodium phosphate, sodium carbonate, calcium hydrogen phosphate, sodium hypophosphite, sodium phosphite, or mixtures thereof.

The above method, wherein said acid catalyst is sodium hypophosphite.

The above method, wherein said polyethylene glycol is selected from the group consisting of polyethylene glycol 200, 400, 600 1500, 4000, 6000, or mixtures thereof.

The above method, wherein said polyethylene glycol is polyethylene glycol 600.

The above method, wherein said cellulose-containing material is cotton gauze, cotton/polyolefin blend or cotton/polyester blend.

The above method, wherein said cellulose-containing material is cotton gauze.

The above method, wherein the amount of alginate crosslinked to the cellulose of said cellulose-containing material in said wound dressings is from about 1 to about 75% by weight of alginate.

The above method, wherein the amount of alginate crosslinked to the cellulose of said cellulose-containing material in said wound dressings is from about 40 to about 60% by weight of alginate.

The above method, wherein the amount of alginate crosslinked to the cellulose of said cellulose-containing material in said wound dressings is about 50% by weight of alginate.

The above method, wherein the aqueous solution further comprises oleic acid.

A wound dressing, said wound dressing prepared by the above method.

The above wound dressing, wherein the amount of alginate crosslinked to the cellulose of said cellulose-containing material in said wound dressings is from about 1 to about 75% by weight of alginate.

The above would dressing, wherein the amount of alginate crosslinked to the cellulose of said cellulose-containing material in said wound dressings is from about 40 to about 60% by weight of alginate.

The above wound dressing, wherein the amount of alginate crosslinked to the cellulose of said cellulose-containing material in said wound dressings is about 50% by weight of alginate.

A method for treating a wound, comprising applying the above wound dressing to the wound.

A wound dressing, comprising or consisting essentially of or consisting of cellulose-containing material and alginate, wherein said alginate is crosslinked through a polycarboxylic acid ester bond to the celluose of said cellulose-containing material.

The above wound dressing, wherein the amount of alginate crosslinked to the cellulose of said cellulose-containing material in said wound dressings is from about 1 to about 75% by weight of alginate.

The above would dressing, wherein the amount of alginate crosslinked to the cellulose of said cellulose-containing material in said wound dressings is from about 40 to about 60% by weight of alginate.

The above wound dressing, wherein the amount of alginate crosslinked to the cellulose of said cellulose-containing material in said wound dressings is about 50% by weight of alginate.

A method for treating a wound, comprising applying the above wound dressing to the wound.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Absorbency and Stretch Properties of Algino-Cellulose Gauze.

| | Thread Count W/F | Alginate-Treated Elasticity* | Untreated Gauze Elasticity | Alginate-Treated Absorbency+ | Untreated Gauze Absorbency |
|---|---|---|---|---|---|
| Gauze A | 31.7/39.1 | 105.07 ± 1.26 | 102.27 ± | 590.33 ± 22.01 | 156.57 ± 2.89 |
| Gauze B | 38.7/34.4 | 110.38 ± 2.31 | 125.44 ± 5.70 | 1032 ± 24.01 | 179.77 ± 8.78 |
| Gauze C | 26.2/32.5 | 111.33 ± 0.38 | 107.14 ± 2.38 | 496.33 ± 3.79 | 146.95 ± 8.97 |
| Gauze D | 33.2/40.9 | 121.24 ± 5.29 | 118.47 ± 0.50 | 212.58 ± 21.52 | 186.65 ± 8.35 |

A Gauze: 12 ply—4 in. × 4 in., USP Type VII gauze, Kendall, Healthcare Products, Mansfield MA;
B Gauze: Sof-Band bulky bandage, Johnson & Johnson;
C Gauze (Kling conforming gauze bandage, Johnson & Johnson;
D Gauze Cheesecloth (cotton) Type III, American Fiber & Finishing Inc, Albemarle, NC.
Gauzes were treated with alginate solution (1–1.5 gm/100 mL) as described in the Materials and Methods section wherein citric acid solutions (0.62M) were combined with sodium hypophosphite solutions (4.0%).
*Standard test method for stretch properties of woven fabrics (ASTM D 3107 B-75) (22).
+Absorbency was tested as outlined in the Materials and Methods section.

I claim:

1. A method for preparing a wound dressing wherein alginate is crosslinked to cellulose through a polycarboxylic acid ester bond, comprising introducing cellulose-containing material into an aqueous solution wherein said aqueous solution comprises water, alginate, a crosslinker, optionally an acid catalyst, and optionally polyethylene glycol to form cellulose-containing material wherein alginate is crosslinked to cellulose through a polycarboxylic acid ester bond, drying, and curing, wherein the amount of alginate crosslinked to the cellulose of said cellulose-containing material in said wound dressings is from about 1 to about 75% by weight of alginate.

2. The method according to claim 1, wherein said alginate is selected from calcium alginate, sodium alginate, potassium alginate, ammonium alginate, and mixtures thereof.

3. The method according to claim 1, wherein said alginate is sodium alginate.

4. The method according to claim 1, wherein said crosslinker is a polycarboxylic acid selected from the group consisting of citric acid, maleic acid, itaconic acid, succinic acid, trans-aconitic acid, cis-aconitic acid, tricarbalyllylic acid, 1,2,3,-benzenetricarboxylic acid, 1,2,4-benzenetricarboxylic acid, 1,2,3,4-butanetetracarboxylic acid, 1,2,3,4-cyclobutanetetracarboxylic acid, all-cis-1,2,3,4-cyclopentanetetracarboxylic acid, tetrahydrofuran-2,3,4,5-tetracarboxylic acid, 1,2,4,5-benzenetetracarboxylic acid, all-cis-1,2,3,4,5,6-cycohexacarboxylic acid, mellitic acid, polymaleic acid, and mixtures thereof.

5. The method according to claim 1, wherein said crosslinker is citric acid.

6. The method according to claim 1, wherein said acid catalyst is selected from the group consisting of lithium hydrogen phosphate, sodium hydrogen phosphate, potassium hydrogen phosphate, lithium hydrogen phosphate, sodium hydrogen phosphate, potassium hydrogen phosphate, sodium phosphate, sodium carbonate, calcium hydrogen phosphate, sodium hypophosphite, sodium phosphite, or mixtures thereof.

7. The method according to claim 1, wherein said acid catalyst is sodium hypophosphite.

8. The method according to claim 1, wherein said polyethylene glycol is selected from the group consisting of polyethylene glycol 200, 400, 600 1500, 4000, 6000, or mixtures thereof.

9. The method according to claim 1, wherein said polyethylene glycol is polyethylene glycol 600.

10. The method according to claim 1, wherein said cellulose-containing material is cotton gauze, cotton/polyolefin blend or cotton/polyester blend.

11. The method according to claim 1, wherein said cellulose-containing material is cotton gauze.

12. The method according to claim 1, wherein the amount of alginate crosslinked to the cellulose of said cellulose-containing material in said wound dressings is from about 40 to about 60% by weight of alginate.

13. The method according to claim 1, wherein the amount of alginate crosslinked to the cellulose of said cellulose-containing material in said wound dressings is from about 50% by weight of alginate.

14. The method according to claim 1, wherein said aqueous solution further comprises oleic acid.

15. The method according to claim 1, wherein said method consists essentially of introducing cellulose-containing material into an aqueous solution wherein said aqueous solution comprises water, alginate, a crosslinker, optionally oleic acid, optionally an acid catalyst and optionally polyethylene glycol to form cellulose-containing material wherein alginate is crosslinked to cellulose through a polycarboxylic acid ester bond, drying, and curing, wherein the amount of alginate crosslinked to the cellulose of said cellulose-containing material in said wound dressings is from about 1 to about 75% by weight of alginate.

16. The method according to claim 1, wherein said method consists of introducing cellulose-containing material into an aqueous solution wherein said aqueous solution comprises water, alginate, a crosslinlcer, optionally oleic acid, optionally an acid catalyst, and optionally polyethylene glycol to form cellulose-containing material wherein alginate is crosslinked to cellulose through a polycarboxylic acid ester bond, drying, and curing, wherein the amount of alginate crosslinked to the cellulose of said cellulose-containing material in said wound dressings is from about 1 to about 75% by weight of alginate.

17. A wound dressing, said wound dressing prepared by the method according to claim 1.

18. The would dressing according to claim 17, wherein the amount of alginate crosslinked to the cellulose of said cellulose-containing material in said wound dressings is from about 40 to about 60% by weight of alginate.

19. The wound dressing according to claim 17, wherein the amount of alginate crosslinked to the cellulose of said cellulose-containing material in said wound dressings is about 50% by weight of alginate.

20. The would dressing according to claim 17, wherein said method consists essentially of introducing cellulose-containing material into an aqueous solution wherein said aqueous solution comprises water, alginate, a crosslinker, optionally oleic acid, optionally an acid catalyst, and optionally polyethylene glycol to form cellulose-containing material wherein alginate is crosslinked to cellulose through a polycarboxylic acid ester bond, drying, and curing, wherein the amount of alginate crosslinked to the cellulose of said cellulose-containing material in said wound dressings is from about 1 to about 75% by weight of alginate.

21. The would dressing according to claim 17, wherein said method consists of introducing cellulose-containing material into an aqueous solution wherein said aqueous solution comprises water, alginate, a crosslinker, optionally oleic acid, optionally an acid catalyst, and optionally polyethylene glycol to form cellulose-containing material wherein alginate is crosslinked to cellulose through a polycarboxylic acid ester bond, drying, and curing, wherein the amount of alginate crosslinked to the cellulose of said cellulose-containing material in said wound dressings is from about 1 to about 75% by weight of alginate.

22. A method for treating a wound, comprising applying a wound dressing as claimed in claim 17 to the wound.

23. A wound dressing, comprising cellulose-containing material and alginate, wherein said alginate is crosslinked through a polycarboxylic acid ester bond to the celluose of said cellulose-containing material, wherein the amount of alginate crosslinked to the cellulose of said cellulose-containing material in said wound dressings is from about 1 to about 75% by weight of alginate.

24. The would dressing according to claim 23, wherein the amount of alginate crosslinked to the cellulose of said cellulose-containing material in said wound dressings is from about 40 to about 60% by weight of alginate.

25. The wound dressing according to claim 23, wherein the amount of alginate crosslinked to the cellulose of said cellulose-containing material in said wound dressings is about 50% by weight of alginate.

26. The wound dressing according to claim 23, wherein said wound dressing consists essentially of cellulose-containing material and alginate, wherein said alginate is crosslinked through a polycarboxylic acid ester bond to the celluose of said cellulose-containing material, wherein the amount of alginate crosslinked to the cellulose of said cellulose-containing material in said wound dressings is from about 1 to about 75% by weight of alginate.

27. The wound dressing according to claim 23, wherein said wound dressing consists of cellulose-containing material and alginate, wherein said alginate is crosslinked trough a polycarboxylic acid ester bond to the celluose of said cellulose-containing material, wherein the amount of alginate crosslinked to the cellulose of said cellulose-containing material in said wound dressings is from about 1 to about 75% by weight of alginate.

28. A method for treating a wound, comprising applying a wound dressing as claimed in claim 23 to the wound.

* * * * *